US010172970B2

(12) United States Patent
Kelly et al.

(10) Patent No.: US 10,172,970 B2
(45) Date of Patent: *Jan. 8, 2019

(54) FEEDBACK LOOP CONTROL OF AEROSOLIZED COMPOUND WITHIN A HUMAN OCCUPIABLE SPACE

(71) Applicant: Prolitec Inc., Milwaukee, WI (US)

(72) Inventors: Craig Kelly, Ellicott City, MD (US); Richard W. Weening, Seattle, WA (US)

(73) Assignee: Prolitec Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/729,477

(22) Filed: Oct. 10, 2017

(65) Prior Publication Data

US 2018/0093006 A1    Apr. 5, 2018

Related U.S. Application Data

(63) Continuation of application No. 13/280,320, filed on Oct. 24, 2011, now Pat. No. 9,789,219, which is a
(Continued)

(51) Int. Cl.
*A61L 9/14* (2006.01)
*F24F 3/16* (2006.01)
*F24F 110/66* (2018.01)

(52) U.S. Cl.
CPC ............ *A61L 9/14* (2013.01); *A61L 2209/111* (2013.01); *F24F 2003/1689* (2013.01);
(Continued)

(58) Field of Classification Search
CPC combination set(s) only.
See application file for complete search history.

(56) References Cited

U.S. PATENT DOCUMENTS 2,591,134 A    4/1952  Canariis
5,924,597 A    7/1999  Lynn
(Continued)

FOREIGN PATENT DOCUMENTS

EP    0 345 149 A2    12/1989
EP    1 609 128 B1    3/2013
(Continued)

OTHER PUBLICATIONS

Baseline-mocon, Inc., "Voc.Traq: USB Toxic Gas Detector & Data Logger," Product Data Sheet, Feb. 3, 2012, 2 pages.

*Primary Examiner* — Kidest Bahta
(74) *Attorney, Agent, or Firm* — Seed IP Law Group LLP

(57) ABSTRACT

A method of maintaining a desired level of an aerosolized compound within a space to be treated with the compound, the method including providing a diffusion device with the compound in liquid form and a control system for operating the device. The control system includes a sensor in fluid communication with the air within the space to be treated configured to sense the concentration of the compound aerosolized within the space. The diffusion device is operated to diffuse the compound into the space. The concentration of the compound within the space to be treated is sensed with the sensor and operation of the diffusion device is altered based on the concentration of the compound sensed to achieve a desired concentration of compound within the space. The sensing and operation altering steps are repeated periodically to maintain the desired concentration of the compound within the space.

11 Claims, 4 Drawing Sheets

Related U.S. Application Data continuation-in-part of application No. 13/090,240, filed on Apr. 19, 2011, now abandoned, which is a continuation-in-part of application No. 11/691,363, filed on Mar. 26, 2007, now Pat. No. 7,930,068.

(60) Provisional application No. 61/405,952, filed on Oct. 22, 2010.

(52) U.S. Cl.
CPC ......... *F24F 2110/66* (2018.01); *Y02A 50/249* (2018.01); *Y02B 30/78* (2013.01)

(56) References Cited

U.S. PATENT DOCUMENTS

| | | | |
|---|---|---|---|
| 6,267,297 B1 | 7/2001 | Contadini et al. | |
| 6,400,996 B1* | 6/2002 | Hoffberg | G05B 19/0426 370/218 |
| 6,712,287 B1 | 3/2004 | Le Pesant et al. | |
| 6,739,479 B2 | 5/2004 | Contadini et al. | |
| 6,790,011 B1 | 9/2004 | Le Pesant et al. | |
| 6,909,972 B2* | 6/2005 | Centanni | G01N 27/221 702/25 |
| 7,326,382 B2 | 2/2008 | Adiga et al. | |
| 7,651,077 B1* | 1/2010 | Rosener | A61L 9/122 239/55 |
| 7,850,931 B2 | 12/2010 | McDonnell et al. | |
| 7,930,068 B2 | 4/2011 | Robert et al. | |
| 8,855,827 B2 | 10/2014 | Weening et al. | |
| 2003/0006899 A1* | 1/2003 | Najmi | G08B 13/1672 340/540 |
| 2003/0175148 A1 | 9/2003 | Kvietok et al. | |
| 2004/0050951 A1 | 3/2004 | Almero | |
| 2004/0184950 A1 | 9/2004 | McVey et al. | |
| 2004/0187950 A1* | 9/2004 | Cohen | C01B 3/00 141/1 |
| 2005/0084415 A1 | 4/2005 | McVey et al. | |
| 2005/0123436 A1 | 6/2005 | Cumberland | |
| 2006/0060990 A1 | 3/2006 | Szpekman | |
| 2006/0078461 A1 | 4/2006 | Kaplan | |
| 2006/0117769 A1 | 6/2006 | Helt et al. | |
| 2006/0140817 A1 | 6/2006 | Cumberland et al. | |
| 2006/0226787 A1 | 10/2006 | Krichtafovitch et al. | |
| 2006/0237090 A1 | 10/2006 | Benalikhoudja | |
| 2007/0082601 A1 | 4/2007 | Desrochers et al. | |
| 2007/0166185 A1 | 7/2007 | Bartels | |
| 2010/0070086 A1* | 3/2010 | Harrod | G05B 19/042 700/276 |
| 2010/0143186 A1 | 6/2010 | Belmonte et al. | |
| 2011/0253797 A1 | 10/2011 | Weening et al. | |
| 2016/0030621 A1 | 2/2016 | Weening et al. | |

FOREIGN PATENT DOCUMENTS

| | | |
|---|---|---|
| JP | 2005-524522 A | 8/2005 |
| WO | 90/12600 A1 | 11/1990 |
| WO | 96/23530 A1 | 8/1996 |
| WO | 2004/080604 A2 | 9/2004 |

\* cited by examiner

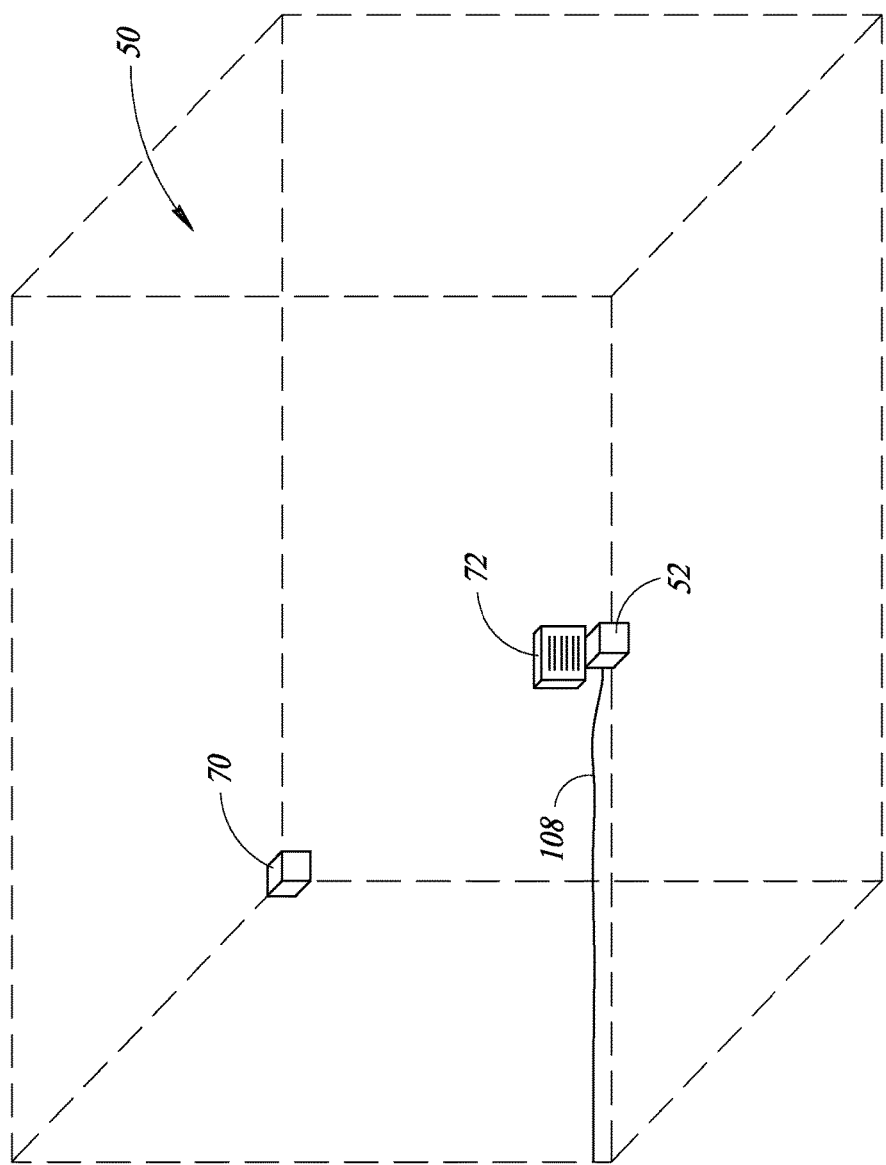

```
┌─────────────────────────────────────────────────────────────┐
│ Providing a diffusion device including a compound to be     │
│ aerosolized from a liquid form and including a control      │
│ system for operating the diffusion device to diffuse the    │
│ compound into the air within an occupiable space to be      │
│ treated, the control system of the diffusion device         │
│ including a sensor in fluid communication with the air      │
│ within the occupiable space to be treated with the          │
│ compound, and the sensor being configured to sense the      │
│ concentration of the compound aerosolized within the        │
│ occupiable space to be treated                              │
└─────────────────────────────────────────────────────────────┘
                              │
                              ▼
┌─────────────────────────────────────────────────────────────┐
│ Operating the diffusion device to diffuse the compound into │
│ the occupiable space to be treated throughout a treatment   │
│ period in which the occupiable space is subjected to        │
│ uncontrolled ventilation rate conditions arising from HVAC  │
│ activity and entry/exit activity                            │
└─────────────────────────────────────────────────────────────┘
                              │
                              ▼
┌─────────────────────────────────────────────────────────────┐
│ Sensing the concentration of the compound within the        │
│ occupiable space to be treated with the sensor and altering │
│ the operation of the diffusion device based on the          │◄─┐
│ concentration of the compound sensed within the occupiable  │  │
│ space if necessary to achieve a desired concentration of    │  │
│ the compound within the occupiable space to be treated      │  │
└─────────────────────────────────────────────────────────────┘  │
                              │                                  │
                              ▼                                  │
┌─────────────────────────────────────────────────────────────┐  │
│ Repeating the sensing and altering step periodically during │  │
│ the treatment period to maintain the desired concentration  │──┘
│ of the compound within the occupiable space to be treated   │
└─────────────────────────────────────────────────────────────┘
                              ┆
                              ▼
┌─────────────────────────────────────────────────────────────┐
│ Optionally monitoring other activity within the occupiable  │
│ space to be treated and altering the operation of the       │
│ diffusion device based on the monitoring of such other      │
│ activity within the occupiable space to be treated          │
└─────────────────────────────────────────────────────────────┘
```

*FIG. 4*

FEEDBACK LOOP CONTROL OF AEROSOLIZED COMPOUND WITHIN A HUMAN OCCUPIABLE SPACE

CROSS-REFERENCE TO RELATED APPLICATIONS

The present application is a continuation of U.S. patent application Ser. No. 13/280,320, filed Oct. 24, 2011, which claims priority to U.S. Provisional Patent Application Ser. No. 61/405,952, filed on Oct. 22, 2010, the disclosures of which are incorporated herein by reference. U.S. patent application Ser. No. 13/280,320 is also a continuation-in-part of U.S. patent application Ser. No. 13/090,240, filed on Apr. 19, 2011, which is a continuation-in-part of U.S. patent application Ser. No. 11/691,363, filed on Mar. 26, 2007, now U.S. Pat. No. 7,930,068, the disclosures of which are incorporated herein by reference.

BACKGROUND

The inactivation of airborne microorganisms as a method of inhibiting the transmission of disease can be achieved through the use of airborne air sanitizers, air disinfectants, and air sterilizers (hereafter disinfectants). Diffusion controlled encounters between airborne microorganisms and disinfectants serves as a basis for inactivation of the microorganism by mechanisms that are microorganism and disinfectant specific.

As a result of the requirement for diffusion controlled encounters between the airborne microorganism and disinfectants, a necessary step in the microorganism inactivation process, the rate of microorganism inactivation by the disinfectant is dependent upon the rate of the microorganism-disinfectant encounters. The rate of the encounters can be represented as a second-order kinetic process. The rate of a second-order event can be defined as a function of the airborne concentrations of the two reacting components, the microorganism and the disinfectant. The airborne concentration of the disinfectant is therefore an important parameter controlling the rate of airborne microorganism inactivation by airborne disinfectant, and therefore the control of the airborne concentration of the disinfectant is critical for any air disinfection process.

BRIEF DESCRIPTION OF THE FIGURES

The accompanying drawing figures, which are incorporated in and constitute a part of the description, illustrate several aspects or embodiments of the invention and together with the description, serve to explain the principles of the disclosure. A brief description of the figures is as follows:

FIG. 3 is a diagrammatic view of an occupiable space 50 to be treated by an aerosolized compound discharged from a liquid diffusion device 52 (including a control system) with the aid of an auxiliary fan 72 and shows a source of pressurized gas 108 coupled to the liquid diffusion device 52 and a sensor 70 provided within the space 50 for detecting the concentration of one or more of the chemical components of the aerosolized compound.

FIG. 4 is a process flow diagram showing one example embodiment of a method of maintaining a desired level of an aerosolized compound within an occupiable space.

DETAILED DESCRIPTION

In the work that resulted in the present disclosure, an aerosol generator was used that produces a controlled output of an airborne disinfectant, which to date has been composed of triethylene glycol or propylene glycol (hereafter glycol). The aerosolized glycol rapidly comes into equilibrium with the gas phase, resulting in an environmentally defined distribution of gaseous and liquid phase glycol distributed within the accessible air volume. In the absence of a sensor feedback loop, the output of glycol from the aerosol generator can only be controlled through indirect methods, e.g., through duty cycle, timed program, or manual on/off mechanisms, while environmental variables can dramatically and dynamically alter the airborne concentration of gaseous glycol. Such approaches to the control of glycol output are described in commonly owned U.S. patent application Ser. No. 11/691,363, now issued as U.S. Pat. No. 7,930,068, the disclosure of which is incorporated herein by reference.

The present disclosure is directed to the development and incorporation of a sensor that is capable of detecting and monitoring the concentration of gas phase glycol into the operation of an airborne disinfectant diffusion device. If a reliable sensor can be identified, then it can be integrated into a suitable control system to enable inhibition or excitation of the aerosol generator output in a manner that would allow the maintenance of a predetermined concentration of glycol vapor within a space to be treated. This would permit efficiency of operation of the device where the appropriate effective concentration is maintained for the desired efficacy without the distribution of an excess amount of disinfectant that may precipitate on top of surfaces in the treated space and possibly be wasteful of the disinfectant.

It is not intended to limit the present disclosure to any particular device for emitting or aerosolizing a glycol or other airborne disinfectant. Whatever method or device is used to distribute the airborne disinfectant through a space to be treated, the concentration of the disinfectant present in the space is to be measured, and the concentration of disinfectant measured can be used to drive the operation of the device or method to distribute more or less disinfectant into the space.

Photoionization detection (PID) detectors were identified which had the capability to photoionize molecules with ionization potentials <10.6 eV; such is an effective method of detecting and monitoring the gas-phase concentration of glycol in the treated space. For verification of the detection capability, a comparison was made against a known device, namely a Baseline®-Mocon®, inc. VOC-TRAQ USB Toxic Gas Detector and Data Logger using a Silver piD-TECH® plus 0.02-20 ppm dynamic range (isobutylene) sensor.

Figure 1:
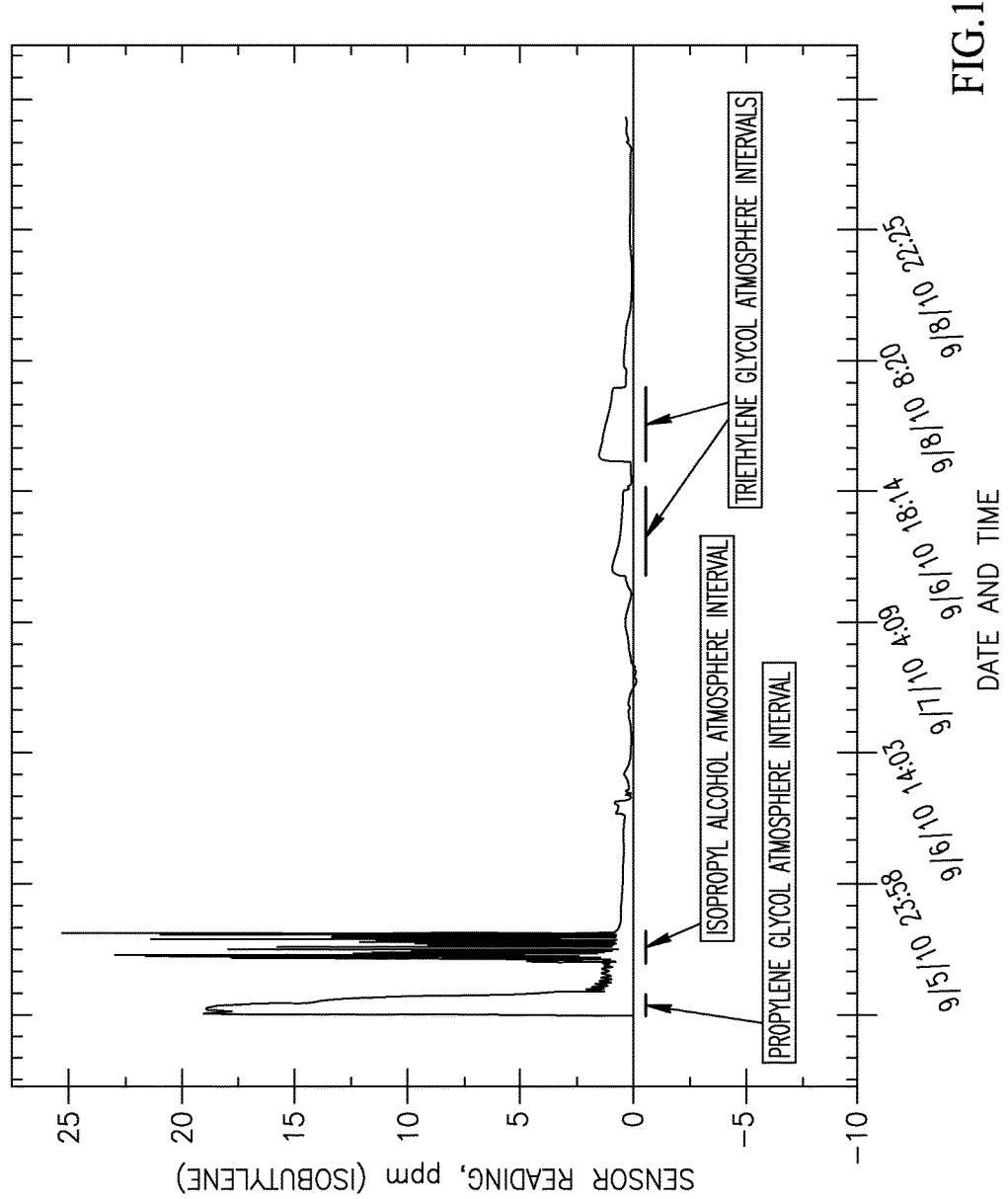
FIG. 1 illustrates concentrations over time of glycol compounds within a space to be treated as determined by a photoionization detection device capable of detecting propylene glycol, isopropyl alcohol, and triethylene glycol with the atmosphere of the space.

FIG. 1 provides experimental verification of the ability to detect propylene glycol, isopropyl alcohol, and triethylene glycol by the PID sensor or detector when the PID detector is exposed to high concentrations of the respective vapors. The figure also provides an indication of baseline noise/variability in an uncontrolled interior environment.

Figure 2:
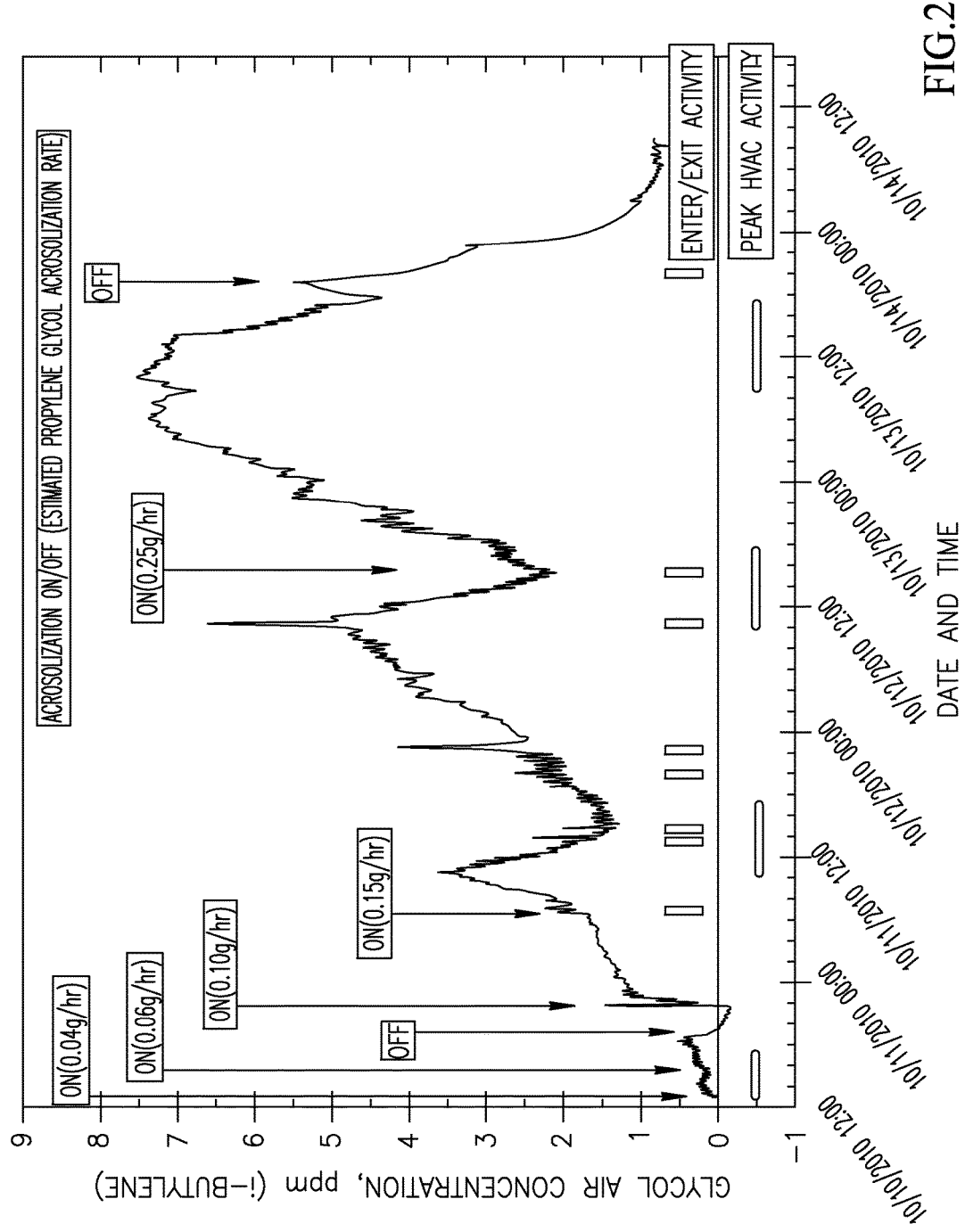
FIG. 2 illustrates the concentration over time of a glycol compound with a space to be treated as determined by a photoionization detection device to show the effect of different activities within the space on the airborne glycol concentration within the space.

Propylene glycol gas-phase concentration was studied under uncontrolled ventilation rate conditions as a function of aerosol generation rate, FIG. 2. In addition to increased sensor readings that correlate with increased aerosol generation rate, low-frequency oscillations are observed that correlate with HVAC activity (air conditioning) and high-frequency oscillations that correlate with room entry/exit activity. When integration is completed, the sensor readings may be used to control the aerosol generation rate to compensate for the baseline variability associated with ventilation rate variability (e.g., HVAC and room entry/exit activity). Additional sensors could be provided in the control system for the operation of the disinfectant diffusion device to respond to such events before the events have an adverse impact on the concentration disinfectant in the space. By way of a non-limiting example, the control system may include a door sensor that would trigger a reaction by the diffusion system when an entry of exit is recorded. Alternatively, the control system may include a detector indicating when the HVAC system feeding the treated space is activated and the nature of the HVAC system's operation (heating, cooling, venting, air or heat exchange, etc.).

It is anticipated that a photoionization detector that is capable of ionizing molecules with ionization potentials of <9.6 eV may also be used within the scope of the present disclosure. The photoionization potential of triethylene glycol is approximately 9.6 eV, and the ionization potential of propylene glycol is assumed to be similar to that for triethylene glycol, or approximately 9.6 eV. If detection at <9.6 eV is as sensitive for glycol detection as at <10.6 eV, the lower ionization potential detector may provide improved selectivity for the glycols by virtue of not detecting potentially interfering molecules greater than about 9.6 eV, thereby eliminating potential contribution to the sensor noise from ionizable volatile organic compounds with ionization potentials in the 9.6-10.6 eV range, which are not the desired disinfectant compounds. If the <9.6 eV detector is unable to detect the glycols, or the sensitivity is greatly reduced, use of a dual detector may be developed to subtract out the <9.6 eV signal to improve the selectivity for the detection of the glycols by virtue of removing potentially interfering signals from easily ionizable volatile organic compounds. Selectivity toward the glycols is therefore expected by one of the two strategies, with success of each dependent upon the precise ionization potential of the glycols and the efficiency of ionization of the glycols by each of the two detectors. Selectivity is potentially of value under conditions of interfering, non-glycol, volatile organic compounds.

Upon finalization of the sensor configuration, as described above, the sensor may be integrated into any sort of aerosol generators to enable a feedback control mechanism facilitating automatic aerosolization rate control for maintenance of a predefined glycol gas-phase concentration. That is, the sensor will serve a function that is comparable to a thermostat for temperature control, except it will maintain the glycol, rather than the heat, level. Such sensor configurations may be used to control operation of a number of different devices that may operate to distribute or diffuse disinfectant within a space to be treated.

It is anticipated that the sensing, analysis and detection of glycol compounds as described herein may be extended to other aerosol organic compounds as well. It is anticipated that similar analysis and evaluation of data received from sensor(s) positioned within a particular space may be used to determine the presence of other airborne organic compounds and also to identify potentially unknown compounds. It is not the intention to limit the present disclosure to solely the identification and evaluation of glycols or to any particular disinfectant compounds.

While aspects of the invention have been described with reference to example embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only; the invention is to be taken as including all reasonable equivalents to the subject matter of the invention, and should not limit the scope of the invention set forth in the following claims.

What is claimed is:

1. A method of maintaining a desired level of an aerosolized compound within a human occupiable space, the method comprising:
    operating a diffusion device to diffuse a compound from a scented liquid source into a human occupiable space to be treated throughout a treatment period in which the human occupiable space is subjected to uncontrolled ventilation rate conditions arising from HVAC activity and from entry/exit activity of human occupants moving into and out of the human occupiable space;
    sensing a concentration of the compound within the human occupiable space to be treated throughout a treatment period in which the human occupiable space is subjected to uncontrolled ventilation rate conditions arising from HVAC activity and from entry/exit activity of human occupants moving into and out of the human occupiable space; and
    altering the operation of the diffusion device based on the concentration of the compound sensed within the human occupiable space if necessary to achieve a desired concentration of compound within the human occupiable space to be treated.

2. The method of claim 1, further comprising:
    repeating the sensing and the altering periodically during the treatment period to maintain the desired concentration of the compound within the human occupiable space to be treated.

3. The method of claim 1, further comprising:
    monitoring other activity within the human occupiable space to be treated; and
    altering the operation of the diffusion device based on the monitoring of such other activity within the human occupiable space to be treated.

4. The method of claim 3 wherein monitoring other activity within the human occupiable space includes monitoring one or more entries or exits of human occupants from the human occupiable space, and wherein altering the operation of the diffusion device includes altering the operation of the diffusion device based at least in part on the monitoring of the one or more entries or exits of the human occupants.

5. The method of claim 3 wherein monitoring the other activity within the human occupiable space includes monitoring HVAC activity, and wherein altering the operation of the diffusion device includes altering the operation of the diffusion device based at least in part on the monitoring of the HVAC activity.

6. The method of claim 3 wherein monitoring other activity within the human occupiable space and altering the operation of the diffusion device includes anticipating changes in concentration of the compound from such other activity and responding to such other activity before the other activity has an adverse impact on the concentration of the compound in the human occupiable space.

7. The method of claim 1 wherein sensing the concentration of the compound within the human occupiable space to be treated includes observing low-frequency oscillations that correlate with HVAC activity and observing high-frequency oscillations that correlate with entry/exit activity.

8. The method of claim 1 wherein altering the operation of the diffusion device includes controlling an aerosol generation rate to compensate for a baseline variability associated with ventilation rate variability.

9. A liquid diffusion system for treating a human occupiable space that is subjected to uncontrolled ventilation rate conditions arising from HVAC activity and from entry/exit activity of human occupants moving into and out of the human occupiable space with a compound aerosolized from a scented liquid, the liquid diffusion system comprising:

a liquid diffusion device including a cartridge filled with the scented liquid;

a sensor in fluid communication with the air in the human occupiable space to be treated, the sensor configured to sense the concentration of the compound within the air of the human occupiable space to be treated irrespective of the presence of human occupants throughout a treatment period in which the human occupiable space is subjected to uncontrolled ventilation rate conditions arising from HVAC activity and entry/exit activity of human occupants moving into and out of the human occupiable space; and a control system for operating the liquid diffusion device to diffuse the compound from the scented liquid into the occupiable space to be treated, the control system configured to alter the operation of the liquid diffusion device based on the concentration of the compound sensed by the sensor within the human occupiable space to be treated and a desired concentration of that compound.

10. The liquid diffusion device of claim 9 wherein the control system includes a feedback loop for the operation of the liquid diffusion device, with the sensor periodically sensing the concentration of the compound and the control system altering operation of the liquid diffusion device based on each sensed concentration of the compound sensed by the sensor.

11. The liquid diffusion device of claim 9 wherein the control system further comprises at least one additional sensor to sense activity within the human occupiable space to be treated and to alter the operation of the liquid diffusion device based on such activity within the human occupiable space sensed by the at least one additional sensor.

* * * * *